United States Patent [19]

Tuunanen et al.

[11] Patent Number: 5,647,994
[45] Date of Patent: Jul. 15, 1997

[54] METHOD AND APPARATUS FOR SEPARATING MAGNETIC PARTICLES FROM A SOLUTION

[75] Inventors: Jukka Tuunanen; Matti Korpela, both of Helsinki, Finland

[73] Assignee: Labsystems Oy, Helsinki, Finland

[21] Appl. No.: 553,600

[22] PCT Filed: Jun. 20, 1994

[86] PCT No.: PCT/FI94/00275

§ 371 Date: Dec. 6, 1995

§ 102(e) Date: Dec. 6, 1995

[87] PCT Pub. No.: WO95/00247

PCT Pub. Date: Jan. 5, 1995

[30] Foreign Application Priority Data

Jun. 21, 1993 [FI] Finland ......................... 932866

[51] Int. Cl.$^6$ ........................................... B01D 35/06
[52] U.S. Cl. .................... 210/695; 210/222; 210/416.1
[58] Field of Search ............................ 210/222, 416.1, 210/695; 209/224, 232; 436/526; 422/100, 101

[56] References Cited

U.S. PATENT DOCUMENTS

| | | | |
|---|---|---|---|
| 3,970,518 | 7/1976 | Giaver | 436/526 |
| 3,985,649 | 10/1976 | Eddelman . | |
| 4,649,116 | 3/1987 | Daty et al. . | |
| 4,751,053 | 6/1988 | Dodin et al. . | |
| 4,855,045 | 8/1989 | Reed | 210/222 |
| 4,895,650 | 1/1990 | Wang . | |
| 5,200,084 | 4/1993 | Liberti et al. . | |
| 5,340,749 | 8/1994 | Fujiwara et al. | 436/526 |

FOREIGN PATENT DOCUMENTS

| | | |
|---|---|---|
| 317286 | 5/1989 | European Pat. Off. . |
| 479448 | 4/1992 | European Pat. Off. . |
| 865002 | 8/1986 | Finland . |
| 86/06493 | 11/1986 | WIPO . |
| 87/05536 | 9/1987 | WIPO . |

*Primary Examiner*—Matthew O. Savage
*Attorney, Agent, or Firm*—Tilton, Fallon, Lungmus & Chestnut

[57] ABSTRACT

The invention concerns a method and apparatus for separating magnetic particles from a solution and transferring them into another solution. The apparatus includes a pipette container, a separation wall defining a separation chamber, and a magnet disposed at one of a first location adjacent an outer side of the separation wall and a second location within the separation chamber. The magnet is adapted to be brought into such a state that a magnetic field is applied to the solution so that the particles will gather onto one of an inner side of the separation wall when disposed in the first location, or on a collection surface of the magnet when disposed in the second location, or so that the magnetic field no longer keeps the magnetic particles on the separation wall or collection surface. The pipette container includes a suction cylinder for drawing the solution into and solution from the pipette container via a jet channel. The invention can be applied within various fields of biotechnology where solid particles are used as a solid phase to bind biomaterial.

8 Claims, 3 Drawing Sheets

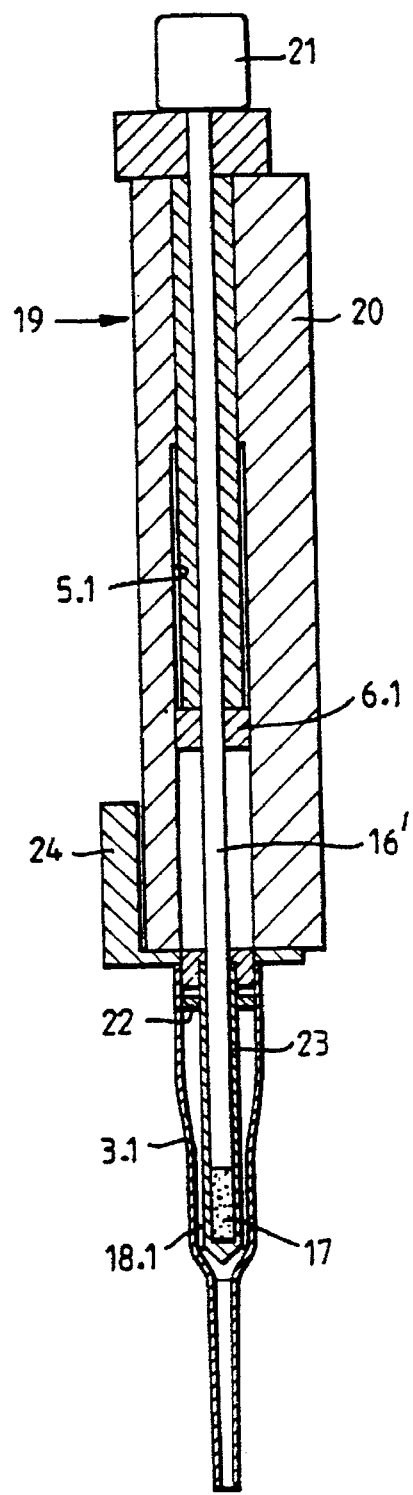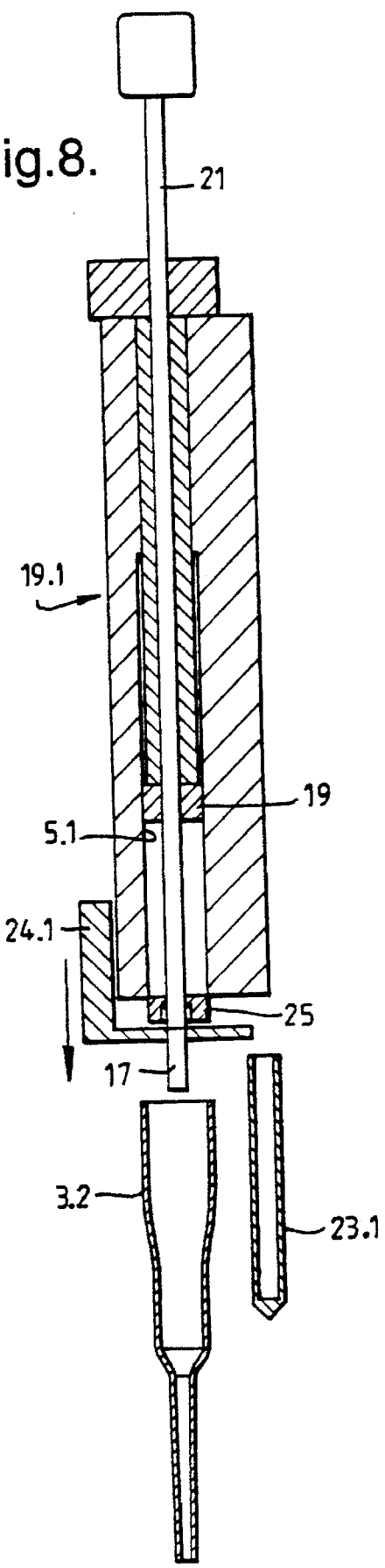

5,647,994

METHOD AND APPARATUS FOR SEPARATING MAGNETIC PARTICLES FROM A SOLUTION

FIELD OF TECHNOLOGY

The invention relates to the separation of biomaterials with the aid of magnetic particles. The invention can be used in applications of many kinds in the fields of biotechnology, biochemistry and biomedicine.

TECHNOLOGICAL BACKGROUND

Polymeric microparticles are used in applications of many kinds as a solid phase to bind biomaterial. Immunoassays, DNA hybridisation, PCR, separation of cells, separation of proteins and cleaning of proteins can be mentioned as examples of such applications.

A large solid phase surface area and short diffusion distances are advantageous features of microparticles.

The size of microparticles is usually in the range 0.05–10 µm. They are available in different materials and pre-activated for many applications. The microparticles are separated from the solution in a centrifugal or filtration process.

Magnetic microparticles are also widely used. Their advantage is that they can be separated from the solution by using an outside magnet, whereby no centrifugal or filtration process is required.

In presently used processes for separating magnetic particles, the reaction vessel is kept in a magnetic field so that the particles gather together and form a so-called pellet on the bottom of the vessel. The solution free of particles is then removed by decantation or suction. The separation of magnetic particles is more simple, quicker and gentler than the separation of conventional particles. However, the solution must be removed very cautiously from the vessel, so that no particles are removed at the same time.

In publication U.S. Pat. No. 4,272,510 magnetic pins, on the tip of which the particles will adhere, are proposed for use for separating macrosized (about 0.1–20 mm) magnetic particles in immunoassays. The particles are removed mechanically from the pins by pushing or by pulling with the aid of stronger magnets located under the vessel.

In publication EP-140787 a method has been proposed, wherein microsized magnetic particles are separated from a solution with the aid of a magnetic rod which is immersed in the solution. The particles are pulled off the rod by using a more powerful magnet.

In publication WO-86/06493 a method has been proposed for use in immunoassays, wherein magnetic particles and an adhered labelled complex are separated from the solution by using a magnetic rod and thereafter removed for measurement. The rod has a fixed magnet and the tip of the rod has a removable protective cover, on the outer side of which the particles adhere. After the separation and before the measurement the protective cover is preferably covered with another protective cover. After the measurement, the covers together with the particles are removed and disposed of and they are replaced-with new protective covers for a new separation. According to the publication, the magnet may also be an electromagnet, in which case the magnetic field can be removed when desired.

In publication WO-87/05536, in turn, a rod provided inside with a vertically movable magnet has been proposed for separating magnetic particles. With the magnet in the bottom position the rod is immersed in a solution containing particles, whereby the particles will gather onto the end of the rod. By allowing the magnet to move to the top position the particles can drop off the rod. In this way particles can be collected and moved from one solution to another.

DESCRIPTION OF THE INVENTION

A method of separation as defined in claim 1 has now been invented. Some advantageous applications of the invention are described the other claims.

In this method a solution containing magnetic particles and material possibly adhered to these is drawn for separation into a container, and separation from the solution is carried out by using a separating means provided with a magnetic element which can be brought into different states. With the aid of this element the effect of the magnetic field can be applied to the solution through a separation wall in the separating means so that the particles will collect onto the separation wall, or the effect of the magnetic field can be turned off so that the particles will not remain on the separation wall, but they will be released into a solution. The solution into which the particles are transferred is usually always a different solution from the one from which they were separated. In some special cases the second solution can be the original solution which has undergone some treatment (for example, a reaction or measurement) while the particles are adhering to the separating means.

In most cases the magnetic element is preferably a movable permanent magnet. However, in some cases it may be preferable to use a fixed magnet and a magnetic field shut-off device which is movable in relation to it. In principle, of course, an electromagnet may also be used.

The separation wall is preferably some kind of hollow body, the outer surface of which comes into contact with the solution and which is provided inside with a magnetic element. To make the separation more efficient, the separation wall may also have a separation area of a suitable shape. However, the outer wall of the container may also function as a separation wall, in which case the magnetic element is located outside it. Hereby the magnetic element may be annular or of some other shape.

To apply the invention, manually operated tools, for example, which function like pipettes may be made. Applicable pipette art is described, for example, in publications FI-47460, FR-2287941, FI-55126, FI-55127, FI-57540, EP-78724 and FI-86812. The tools may also be electrically powered.

To apply the invention, an accessory can also be made which contains the magnetic element and which is used together with a conventional pipette. The accessory could be a rack, for example, where the pipette is placed while separation takes place, or it could be an additional part which is attached to the pipette.

To apply the invention, various one- or multichannel sets of automatic equipment can be made. It may also be used as a component in different kinds of equipment and systems.

The invention may be applied in particular to the separation of microsized particle masses. Paramagnetic particles are preferably used, whereby their redetachment from the separating means is easier.

According to the invention, the separation of magnetic particles and their release into the solution is simpler, quicker and more complete than with any known method. In addition, the invention is applicable both to manually operated and to automatic equipment.

In the following some advantageous applications of the invention are desribed in greater detail. In the drawings of the description:

FIG. 7 shows a device provided with a fourth separating means in accordance with the invention;

FIG. 8 shows a device provided with a fifth separating means in accordance with the invention.

Figure 1:
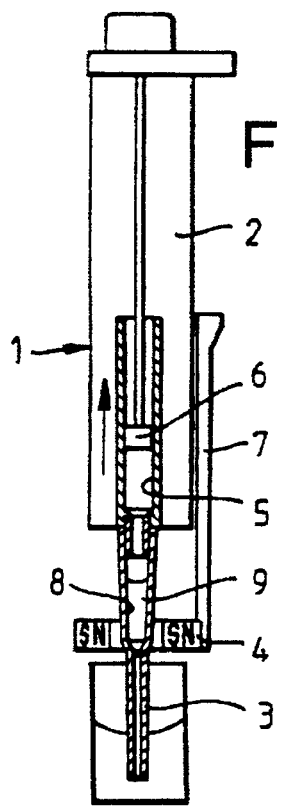
FIGS. 1 and 2 show a device according to the invention provided with a separating means in accordance with the invention.
Figure 2:
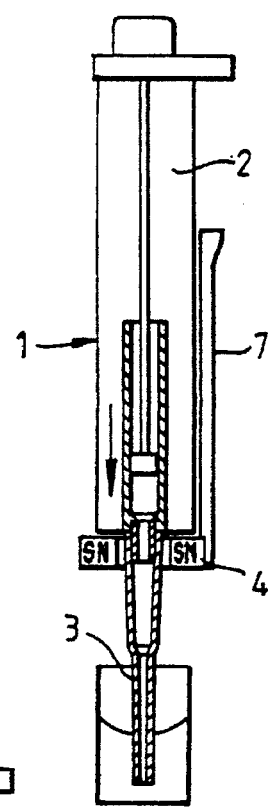
Figure 3:
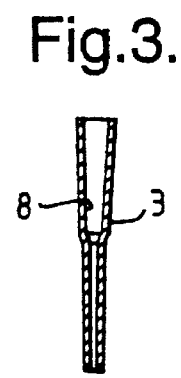
FIG. 3 shows a part of the device in FIGS. 1 and 2.

In the separating means 1 shown in FIGS. 1 and 2, handle 2 contains a pipette jet 3 and a movable annular magnet 4 outside it. The jet is mounted to the bottom end of cylinder 5 in the handle, so that suction or pressure is obtained in the jet with the aid of piston 6 movable within the cylinder.

Magnet 4 is mounted to a movable element 7 in the handle, which is a rod or any similar device used to move the magnet in a vertical direction.

In pipette jet 3 there is a jet channel having a narrower inside diameter, and is a wider container above it. The bottom part of the container constitutes a separation area 8 at the level of which the magnet 4 is in its lower position. To separate magnetic particles 9 from the solution, the solution is drawn into the jet with the magnet in its lower position. The particles will then adhere to the inner jet surface in the separation area where they will remain even when the solution is removed. If desired, another solution may be drawn into the jet, for example, to perform washing or a reaction. To release the particles from the separation area, the magnet is pulled to its upper position. If desired, the particles can be removed from the jet together with the liquid.

Pipette jet 3 can always be replaced when desired.

Figure 4:
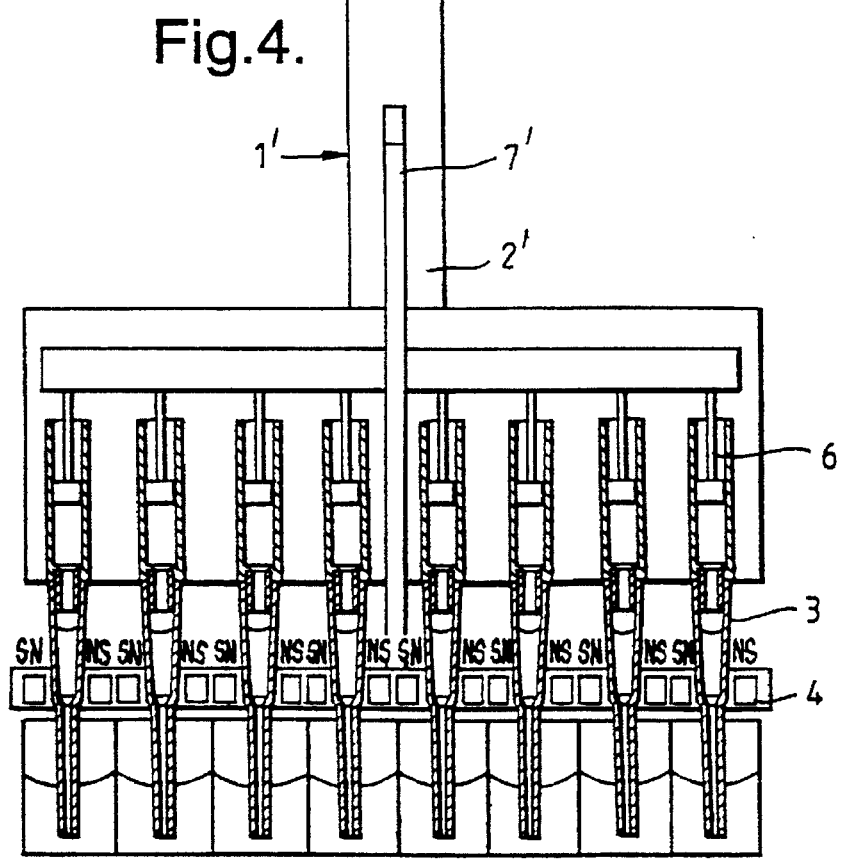
FIG. 4 shows another device provided with the separating means shown in FIGS. 1 and 2.

FIG. 4 shows a multichannel separating device 1' equipped with eight pipette jets 3 located in parallel. On the outer surface of each jet there is a magnet 4 and the magnets are moved at the same time with one and the same rod 7' located in handle 2'. Pistons 6 also have a common moving means.

The multichannel separating device may also be embodied in such a way, for example, that a common magnet for the jets is located between adjacent jets.

Figure 5:
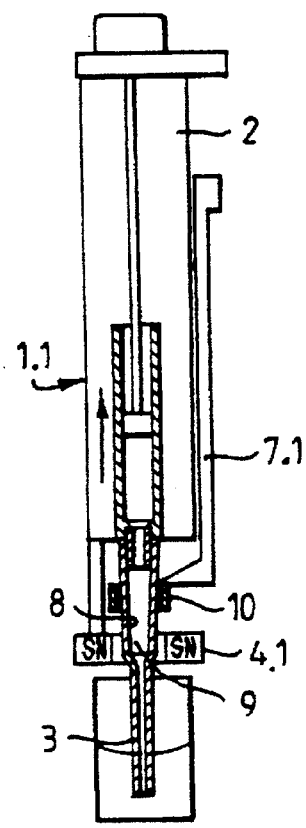
FIG. 5 shows a device provided with another separating means in accordance with the invention.

In the separating device 1.1 according to FIG. 5, an annular magnet 4.1 is attached to handle 2 outside pipette jet 3. Here, however, the magnet is fixed at separation area 8. In addition, on the outer jet surface there is a vertically movable metal bushing 10 of a smaller diameter which fits in between the magnet and the jet. The handle has a means 7.1, such as a lever or any similar means, to move the metal bushing. Otherwise the construction is similar to that of the device shown in FIGS. 1 and 2. The metal bushing is such that when located between the magnet and the jet it prevents the magnet's field from affecting the particles in the jet. When the metal bushing is in its upper position the magnet keeps the particles in the separation area.

Figure 6:
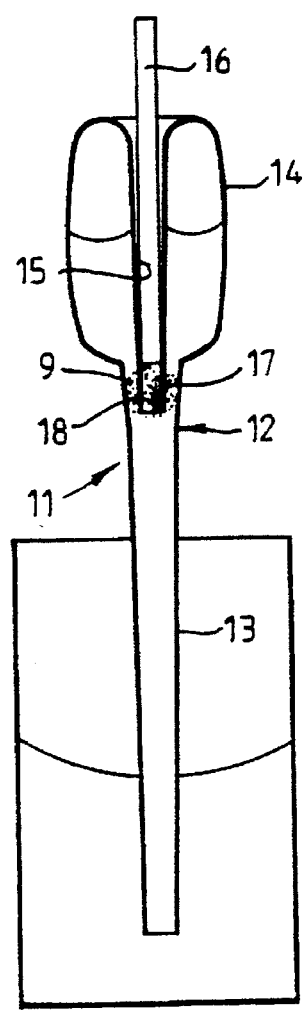
FIG. 6 shows a third separating means in accordance with the invention.

FIG. 6 shows the invention applied to a so-called Pasteur pipette. Separating device 11 has a pipette 12 containing a jet channel 13 open at its bottom end and with an elastic container 14 in its top end. In the top end of the container the outer surface has a narrow well-like recess 15 where the bottom extends up to the top end of the jet channel. The recess contains a movable rod 16 with a magnet 17 at its lower end.

When container 14 is compressed, jet channel 13 introduced into the liquid and the container is allowed to restore its shape, so that liquid is drawn into the pipette. When rod 16 is in its lower position magnetic particles 9 in the liquid will adhere to the inner surface of the container in separation area 18 at the lower end of recess 15. To release the particles, the rod is raised to its upper position.

In the separating device 19 shown in FIG. 7 there is a handle 20 provided with a cylinder 5.1 containing a movable piston 6.1. A movable magnetic rod 16' sealed into the piston and provided with a magnet 17 at its lower end is movable within the piston. The magnetic rod is moved with the aid of a knob 21 located above the piston knob. The lower end of the rod extends outside the cylinder. Jet 3.1 is mounted tightly at the lower end of the cylinder so that suction or pressure can be brought about in the jet by using the piston. Inside jet radial ribs 22 mount a well-like protective cover 23, which fits around the lower end of the rod when the jet is mounted to the cylinder. When the magnetic rod is in its lower position, any magnetic particles contained in the liquid will collect within separation area 18.1. The jet is removed from the cylinder by using remover 24.

Jet 3.1 contains a narrower jet channel and above this a slightly wider separating part at separation area 18.1 and an even wider container part in the top end. The protective cover has a jet extending all the way to the jet channel. The jet and protective cover have been designed to promote separation of the particles and to complete removal of the liquid.

The separating means 19.1 according to FIG. 8 is an application of the separating means 19. Here protective cover 23.1 is separate from jet 3.2. The cover is mounted within cylinder 5.1 using a suitable means 25, such as a bushing, so that the cylinder is not closed. This means has the advantage that the jet can be replaced independently of the protective cover, for example, when particles are adhering to the cover. It is also easier to make the jet and the protective cover separately. In principle, remover 24.1 can be constructed to function in two steps, so that it removes the jet and the cover one after the other. However, it is preferable to provide the protective cover with a separate remover, which is preferably operated by the same push-button as the piston or the rod.

Figure 9:
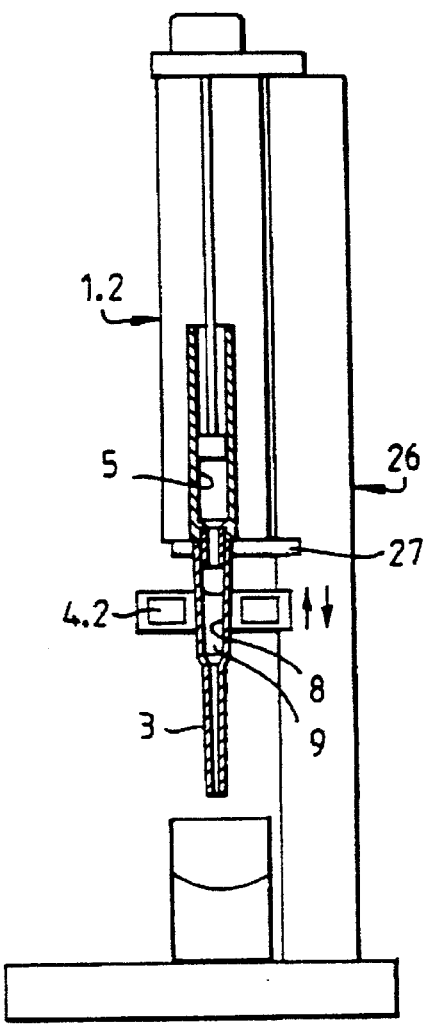
FIG. 9 shows a device provided with a sixth separating means in accordance with the invention.

The application according to FIG. 9 is similar to the separating device shown in FIGS. 1 and 2, but it has a separate rack 26 with movable magnetic elements 4.2. Separating device 1.2 has a pipette jet 3, into which the liquid is drawn for treatment. The rack is provided with a holder 27, which can be used for holding the pipette so that the magnetic element pulls the magnetic particles 9 onto the inner surface of the pipette jet within separation area 8. The liquid can then be removed from the jet so that the particles remain within the jet.

The magnetic element used in the invention may comprise two magnets one on top of the other so that similar poles are opposite to each other (SN-NS). In this way a powerful change of the magnetic field is achieved at the juncture of the magnets to bring about a favourable situation for pulling the particles to this place. Correspondingly, the outer field of the magnetic couple will become weaker vertically, whereby the particles will gather more easily only at the places where the magnets are located. In a similar fashion several magnets can be placed one after the other. This is advantageous when a narrow structure is desired.

We claim:

1. A method of separating magnetic particles from a first solution containing said particles and of transferring said particles to a second solution comprising the steps of:

providing a tubular member defining a separation chamber serially connected to a jet channel, wherein said jet channel defines a flow port at a free end of said tubular member and said jet channel has a diameter that is less than a diameter of said separation chamber;

providing a magnetic element for generating a magnetic field;

drawing said first solution through said jet channel via said flow port into said separation chamber, said separation chamber being defined by a tubular separation wall of said tubular member having an inner side of which comes into contact with said first solution and an outer side;

disposing said magnetic element at one of a first location adjacent an outer side of said separation wall and a second location within said separation chamber;

activating said magnetic element such that said particles under the influence of said field of said magnetic element will collect on the side of said first solution onto one of the inner side of said separation wall when disposed in said first location and a collection surface of said magnetic element when disposed in said second location;

removing said first solution through the jet channel via said flow port after the step of activating said magnetic element;

drawing said second solution into said container through said flow port via said jet channel after the step of removing said first solution;

deactivating said magnetic element such that the magnetic field of said magnetic element no longer keeps said particles on one of the inner surface of said separation wall when disposed in said first location and on said collection surface when disposed in said second position after the step of drawing said second solution.

2. A separating means for separating magnetic particles from a first solution containing particles and for transferring said particles into a second solution comprising:

a tubular member having a first portion defining a separation chamber serially connected to a jet channel, wherein said jet channel defines a flow port at a free end of said tubular member and said jet channel has a diameter that is less than a diameter of said separation chamber;

wherein said separation chamber is defined by a tubular separation wall of said tubular member having an inner side of which comes into contact with said first solution and an outer side;

a magnetic element disposed at one of a first location adjacent the outer side of said separation wall and a second location within said separation chamber, wherein said magnetic element is adapted to be brought into such a state that a magnetic field is applied to said first solution so that said particles under the influence of magnetic field will gather onto one of the inner side of said separation wall on the side of the solution when disposed in said first location and a collection surface of said magnetic element when disposed in said second location, or into such a state that said magnetic field no longer keeps said particles on the inner side of said separation wall when disposed in said first location and the collection surface when disposed in said second location; and wherein said tubular member includes a second portion defining a cylindrical channel serially connected to said separation chamber on a side remote from said jet channel, said cylindrical channel receiving a movable piston thereby defining a suction cylinder for drawing the liquid into said separation chamber and for removing said liquid from said separation chamber through said jet channel via said flow port.

3. The separating means according to claim 2, further including means for removably mounting said first portion of the tubular member to said second portion of the tubular member.

4. The separating means according to claim 3, wherein said collection surface is defined by a tubular cover member having an outer surface for contact with the solution and which contains said magnetic element therein.

5. The separating means according to claim 4, further including means for removably mounting said tubular cover member to said second portion of the tubular member.

6. The separating means according to claim 2, further including means for movably mounting said magnetic element in relation to said separation chamber.

7. The separating means according to claim 2, further including means for fixedly mounting said magnetic element at a location adjacent the outer side of said separation wall, magnetic field shut-off means for disposal in a third location between said magnetic element and said separation wall, and means for moving said magnetic field shut-off means into and out said third location, whereby said magnetic field-shut off means blocks said magnetic field and releases said magnetic particles when disposed in said third location.

8. The separating means according to claim 2, wherein said magnetic element comprises a permanent magnet.

\* \* \* \* \*